United States Patent
Stout

(10) Patent No.: US 9,427,352 B2
(45) Date of Patent: Aug. 30, 2016

(54) HYDRATION PREVENTION COATING

(71) Applicant: Bayer HealthCare LLC, Whippany, NJ (US)

(72) Inventor: Christopher A. Stout, San Bruno, CA (US)

(73) Assignee: Bayer HealthCare LLC, Whippany, NJ (US)

(*) Notice: Subject to any disclaimer, the term of this patent is extended or adjusted under 35 U.S.C. 154(b) by 421 days.

(21) Appl. No.: 13/842,999

(22) Filed: Mar. 15, 2013

(65) Prior Publication Data

US 2014/0276915 A1  Sep. 18, 2014

(51) Int. Cl.

| | | |
|---|---|---|
| *A61B 17/08* | (2006.01) | |
| *A61F 6/20* | (2006.01) | |
| *A61L 31/04* | (2006.01) | |
| *A61L 31/10* | (2006.01) | |
| *A61L 31/14* | (2006.01) | |
| *A61L 31/08* | (2006.01) | |
| *A61F 6/22* | (2006.01) | |

(52) U.S. Cl.
CPC ............... *A61F 6/202* (2013.01); *A61F 6/225* (2013.01); *A61L 31/04* (2013.01); *A61L 31/08* (2013.01); *A61L 31/10* (2013.01); *A61L 31/145* (2013.01); *A61F 6/20* (2013.01); *A61F 6/22* (2013.01); *A61L 2420/02* (2013.01)

(58) Field of Classification Search
CPC ............ A61F 6/20; A61F 6/22; A61F 6/202; A61F 6/225; A61L 31/08; A61L 31/145
See application file for complete search history.

(56) References Cited

U.S. PATENT DOCUMENTS

| | | | |
|---|---|---|---|
| 6,526,979 B1 | 3/2003 | Nikolchev et al. | |
| 6,634,361 B1 | 10/2003 | Nikolchev et al. | |
| 2001/0027299 A1 | 10/2001 | Yang | |
| 2005/0192616 A1 | 9/2005 | Callister et al. | |
| 2007/0056591 A1 | 3/2007 | McSwain | |
| 2011/0094519 A1 | 4/2011 | Gopal | |
| 2014/0221561 A1* | 8/2014 | Spilman .............. | C08G 63/676 524/539 |

OTHER PUBLICATIONS

International Search Report and Written Opinion of the International Searching Authority for corresponding International Application No. PCT/US2014/019820, mailing date Jun. 20, 2014, 9 pages.

* cited by examiner

*Primary Examiner* — Robert Lynch
(74) *Attorney, Agent, or Firm* — Aseem V. Mehta

(57) ABSTRACT

Occlusion devices and delivery systems are described in which a polymerizing oil is used to protect a hydrogel from premature swelling. In an embodiment, a delivery system includes an occlusion device releasably coupled within a catheter sheath. The occlusion device includes an expandable implant and a hydrogel. An at least partially oxidized polymerizing oil is inside a lumen of the catheter sheath between the distal end of the catheter sheath and the hydrogel.

18 Claims, 10 Drawing Sheets

HYDRATION PREVENTION COATING

FIELD

Embodiments of the present invention relate to the field of delivery systems for delivering an occlusion device and, in particular, delivery systems including a hydration prevention coating.

BACKGROUND

Contraception and sterilization may be accomplished by inserting an occlusion device into a reproductive lumen such as fallopian tube or vas deferens. Devices, systems, and methods for such contraceptive approaches have been described in various patents and patent applications assigned to the present assignee. For example, U.S. Pat. No. 6,526,979 and U.S. Pat. No. 6,634,361 describe devices that are transcervically inserted into an ostium of a fallopian tube and mechanically anchored within the fallopian tube. The occlusion devices described in those patents may promote tissue-ingrowth around and within the occlusion device to achieve permanent occlusion and contraception. One example of such a device is known as "Essure" from Conceptus, In. of Mountain View, Calif. Tissue in-growth is not immediate, and up to several months after insertion of the Essure device may be required for tissue in-growth to completely occlude a fallopian tube and for the occlusion devices to be permanently effective.

Other occlusion devices have been described which are designed to achieve immediate or near immediate occlusion, and thereby contraception, upon insertion in the reproductive lumen. For example U.S. Publication No. 2005/0192616 describes an occlusion device including both permeable and impermeable components where the permeable components are designed for tissue in-growth to provide permanent occlusion and effectiveness, and the impermeable components are impermeable to the passage of sperm or egg cells to provide immediate effectiveness. Other applications employ a hydrogel to provide immediate effectiveness. For example, U.S. Publication No. 2011/0094519, assigned to the present assignee, and U.S. Publication No. 2007/0056591 describe occlusion devices including a hydrogel that provides near immediate occlusion upon insertion in the reproductive lumen. U.S. Publication No. 2011/0094519 additionally describes coating a distal end of a delivery catheter sheath with a hydrophobic coating to prevent the hydrogel on the occlusion device from swelling before the occlusion device is delivered to the target site in the reproductive lumen. The coating can be bioabsorbable, biodegradable, or pierced by the occlusion device.

DETAILED DESCRIPTION

Figure 1A:
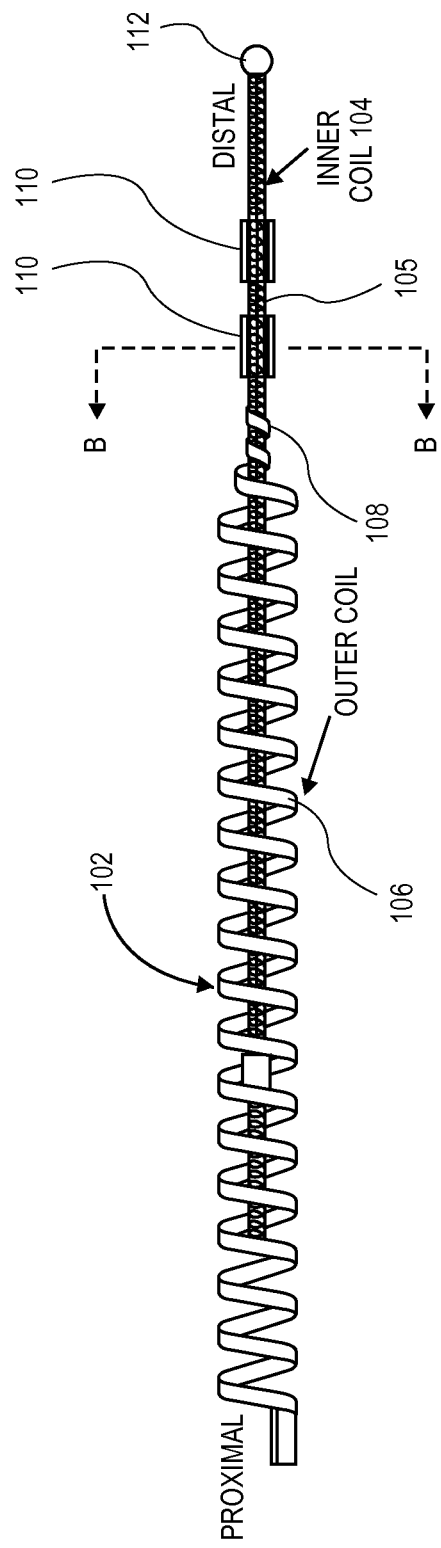
FIG. 1A is a side view illustration of an occlusion device including a pair of hydrogel sleeves on an expandable implant in accordance with an embodiment of the invention.

Embodiments of the invention describe delivery systems and methods for delivering an occlusion device in which a polymerizing oil is used to protect a hydrogel from premature swelling. Various embodiments and aspects will be described with reference to details discussed below and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present invention.

In one embodiment, a delivery system includes a catheter sheath and an occlusion device releasably coupled within the catheter sheath, and the occlusion device includes an expandable implant and a hydrogel on the expandable implant. In accordance with embodiments of the invention, the polymerizing oil caps a portion of the catheter sheath distal to the hydrogel on the expandable implant within the catheter sheath, or coats the hydrogel itself. In accordance with embodiments of the invention, the polymerizing oil is at least partially oxidized and forms a cross-linked skin that protects the hydrogel from premature swelling.

In one aspect, the polymerizing oil and skin create a hydration barrier that prevents the hydrogel from prematurely swelling when the portion of the delivery system including the hydrogel is in contact with a physiological environment. Specifically, the polymerizing oil and skin thereof may protect the hydrogel from premature swelling when tracking the occlusion device to the target deployment site within a body lumen, such as a reproductive body lumen. In one embodiment, the water repellent nature of the polymerizing oil confers a liquid barrier property to the polymerizing oil, while the skin confers a stability to the polymerizing oil and keeps it in place when tracking the occlusion device. In one embodiment, the polymerizing oil is linseed oil, and the water repellent hydrocarbon nature of the C18 fatty acids in the oil help confer the barrier property, while the auto-oxidized skin confers the stability to the polymerizing oil.

In one aspect, embodiments of the invention describe a system in which a skin can be formed from the polymerizing oil in ambient conditions. In this manner, while not precluding additional processing operations, formation of the skin at ambient conditions allows for a simplified application and curing process that does not require a separate curing step to effect skin formation. In other embodiments, cure can be aided by a variety of manners, including thermal and inclusion of drying agents.

In one aspect, the cross-linked skin provides a thermally stable hydration barrier that does not migrate. In this manner, the solid cross-linked skin keeps the hydration barrier in place and resists migration over time and due to temperature changes associated with normal storage and handling of the delivery system.

In yet another aspect, the hydration barrier formed by the polymerizing oil and skin do not substantially affect the flexibility profile of the delivery system. In this manner, the hydration barrier can be applied to the delivery system after the formation and integration of the system components that are designed for specific flexibilities to track tortuous pathways of specific body lumens, and without requiring altering of the design of those system components to maintain a desired flexibility profile. Thus the hydration barrier may be applied to a variety of existing systems without substantially requiring redesign of system flexibility.

Referring now to FIG. 1A a side view illustration is provided of an occlusion device including a pair of hydrogel sleeves on an expandable implant in accordance with an embodiment of the invention. As shown, the expandable implant 102 can be formed from one or more metals or polymers and can include fibers to act as a tissue ingrowth promoting agent to cause tissue to grown into the implant after it has been implanted into a body lumen. For example, the fiber may be polyester, polyethylene terephthalate (PET), or the like, and can be attached to one or more components of the implant, such as the inner coil 104 or outer coil 106. The outer coil 106 may be resilient and self-expanding so that it may be restrained within a catheter sheath and once deployed can radially expand to resiliently engage the walls of the body lumen. A delivery shaft or wire in the delivery system can be removably attached to a proximal end of the inner coil 104. A connection between the proximal end of the inner coil 104 and a delivery shaft or wire can be a number of connections including screw threading or friction fitting that allow the delivery shaft or wire to be removable coupled to the expandable implant 102. The inner coil 104 and outer coil 106 can be connected together by a connection mechanism 108 which can be a solder joint. Alternatively, a segment of the outer coil is tightly wrapped around the inner coil 104 to form the connection mechanism.

In one implementation of manufacture, one or more preformed hollow cylinders of hydrogel, such as hydrogel cylinders 110 are applied onto the distal end of the inner coil 104 prior to applying the distal ball 112. The application of the hydrogel cylinders 110 onto the distal end of the inner coil may be accomplished by sliding the hydrogel cylinders 110 over the distal end of the inner coil in a dehydrated state so that they are not swollen. A glue can be applied between the hydrogel cylinders 110 and the inner coil 104, as well as between the hydrogel cylinders 110 in order to secure the hydrogel cylinders in place. For example, the glue can be applied to the inner coil 104, to the hydrogel cylinders 110, or both. The glue can be applied before or after sliding the hydrogel cylinders onto the inner coil, or can be applied both before and after.

In one embodiment, the glue can be cyanoacrylate such as LOCTITE® 4541 or 431 or 3211 or a mixture of cyanoacrylate glues from Henkel Corporation. The glue can be cured with or without UV (ultraviolet) light. The glue can be selected to enhance the structural integrity or strength of the hydrogel after the glue has been cured. The hydrogels 110 can be applied onto the inner coil 104 without glue in some embodiments.

In the particular embodiment illustrated, a region 105 of the inner coil 104 distal to the outer coil 106 is stretched prior to applying the hydrogels 110. In this manner the winding density (number of winds per unit length) is less in the stretch region 105 of the inner coil 104 than for surrounding regions of the inner coil. In one embodiment, the hydrogels 110 are applied onto the inner coil so that they each span a portion of the stretched region 105, for example, the proximal and distal portions of the stretched region 105. Each hydrogel 110 may also span a portion of the inner coil 104 adjacent the stretched region 105 so that they each span both stretched and unstretched regions of the inner coil 104. In one embodiment, applying the hydrogels over the stretched region allows more area for the glue to penetrate into the inner coil and ensure the glue wets the inside diameter of the hydrogels 110. In one embodiment, the application of the deswollen hydrogels 110 may tend to increase the stiffness of the occlusion device where the hydrogels are located. By stretching the region 105 of the inner coil 104 adjacent the hydrogels, this may have the effect of reducing the stiffness of the inner coil 104 in this region, thereby resulting in a negligible net stiffness change in the regions of the hydrogels 110 compared to a similar inner coil 104 region that has not been stretched and does not include hydrogels.

After applying the hydrogel cylinders 110 onto the inner coil 104, distal ball 112 can be attached to the coil 104 (for example, by soldering or by gluing the ball 112 onto the distal end of the coil 104). In an alternative embodiment, the ball 112 can be attached to the coil 104 before the hydrogels 110 are applied onto the coil (e.g. if the inner diameter of the hydrogels 110 are larger than the outer diameter of the distal ball 112, or if the hydrogels are applied by wrapping a hydrogel sheet around the coil).

Figure 1B:
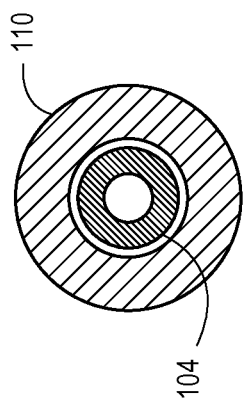
FIG. 1B is a cross sectional side view taken along line B-B of FIG. 1A in accordance with an embodiment of the invention.

FIG. 1B shows a cross-sectional view of the occlusion device (shown in FIG. 1A) taken along the line B-B. This cross-sectional view shows that a hydrogel 110 concentrically surrounds the inner coil 104. The hydrogels 110 can be formed or cast to fit snugly or loosely around the inner coil 104, and a layer of glue may exist at the interface or gap between the inner coil 104 and the inner diameter of the hydrogels 110.

The hydrogel can provide immediate or near immediate sterilization by swelling in a physiological environment once the occlusion device with hydrogel is deployed, and the tissue in-growth promoting agent (such as polyester or PET fibers) promotes in-growth of tissue to permanently occlude the body lumen into which the occlusion device is implanted. Hydrogels may be formed from covalently or non-covalently cross-linked materials, and may be non-degradable ("biostable") in a physiological environment or broken down (biodegradable) by natural processes within the body, referred to as biodegradable or bioabsorbable. The breakdown process may be due to one of many factors in the physiological environment, such as enzymatic activity, heat, hydrolysis, or others, including a combination of these factors.

Hydrogels that are cross-linked may be cross-linked by any of a variety of linkages, which may be reversible or irreversible. Reversible linkages may be due to ionic interaction, hydrogen or dipole type interactions or the presence of covalent bonds. Covalent linkages for absorbable or degradable hydrogels may be chosen from any of a variety of linkages that are known to be unstable in an animal physiological environment due to the presence of bonds that break either by hydrolysis (e.g., as found in synthetic absorbable sutures), enzymatically degraded (e.g., as found in collagen or glycosamino glycans or carbohydrates), or those that are thermally labile (e.g., azo or peroxy linkages).

All of the hydrogel materials appropriate for use in embodiments of the present invention should be physiologically acceptable and should be swollen in the presence of water. These characteristics allow the hydrogels to be introduced into the body in a "substantially deswollen" state and over a period of time hydrate to fill a void, a defect in tissue, or create a hydrogel-filled void within a tissue or organ by mechanically exerting a gentle force during expansion.

"Substantially deswollen" is defined as the state of a hydrogel wherein an increase in volume of the hydrogel of the article or device formed by such hydrogel is expected on introduction into the physiological environment. Thus, the hydrogel may be in a dry state, or less than equilibrium hydrated state, or may be partially swollen with a pharmaceutically acceptable fluid that is easily dispersed or is soluble in the physiological environment. The expansion process also may cause the implanted hydrogel to become firmly lodged within a hole, an incision, a puncture, or any defect in tissue which may be congenital, diseased, or iatrogenic in origin, occlude a tubular or hollow organ, or support or augment tissue or organs for some therapeutic purpose.

Figure 2:
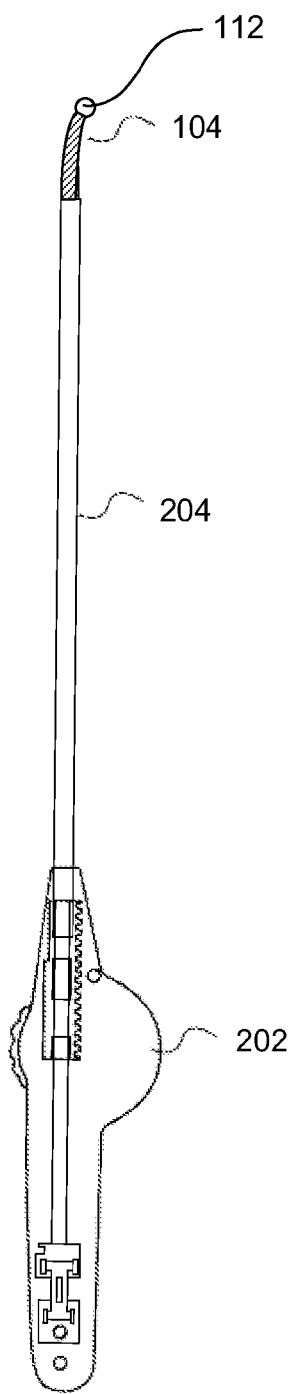
FIG. 2 is a schematic side view illustration of a delivery system in accordance with an embodiment of the invention.

FIG. 2 is a schematic side view illustration of a delivery system in accordance with an embodiment of the invention. As shown, the delivery system 200 may include a control device, such as a handle 202, and a catheter sheath 204 extending distally from the handle 202. In the particular embodiment illustrated, a distal end of the expandable implant including the distal ball 112 and inner coil 104 extends distally beyond the distal end of the catheter sheath 204. As described in further detail below, the distal portion of the expandable implant protruding from the catheter sheath 204 may aid in tracking the delivery system 200 through tortuous body lumens. In accordance with another embodiment, the expandable implant is entirely contained within the catheter sheath 204.

In accordance with embodiments of the invention, at least two approaches may be used to protect the one or more hydrogels from hydrating prior to the occlusion device being properly placed at the target deployment site. In one implementation, the hydrogel itself can be coated with a polymerizing oil. In another implementation, the distal end of the catheter sheath can be capped with a polymerizing oil to prevent liquid from entering through the distal end of the catheter sheath. In yet another embodiment, a polymerizing oil can both cap the distal end of the catheter sheath and partially or fully coat the hydrogel. In accordance with embodiments of the invention, the polymerizing oil is at least partially oxidized and forms a cross-linked skin that forms a seal around the hydrogels or seals the distal end of the catheter sheath to protect the one or more hydrogels from premature swelling. Furthermore, the cross-linked skin can keep the polymerizing oil in place and prevent migration of the seal, while still maintaining the level of flexibility of the delivery system prior to applying the polymerizing oil.

In accordance with embodiments of the invention, polymerizing oils may be at least partially oxidized when exposed to ambient environment (room atmosphere, temperature, pressure). For example, oxidation may result in the formation of a hardened cross-linked skin on the exterior of the polymerizing oil, or the portion of the polymerizing oil that is exposed to the ambient environment due to autoxidation, or the addition of oxygen to an organic compound and subsequent cross-linking. The cross-linked skins that form may be elastic, yet not flow or deform readily. In some embodiments, the interior portion of the polymerizing oil encapsulated by the hardened elastic skin may remain in a liquid state. In other embodiments, oxidation and skin formation can be controlled by exposure to a controlled temperature, pressure, or oxygen content for a determined period of time.

In an embodiment, the polymerizing oil is a drying oil. Drying oils may in general be characterized as being fatty oils containing glycerin in combination with a fatty acid, and liquid at room temperature. Fatty oils are insoluble in water, but are soluble in several organic solvents. Fatty oils occur in many plant families and are stored in seeds and somewhat in fruits, tubers, stems and other plant organs. Extraction of fatty oils is generally performed with solvents, followed by filtering and further purification.

In an embodiment, the drying oil is characterized by the percent of unsaturated fatty acid. Drying oils can be further characterized as being conjugated oils (i.e. alternating single and double bonds), non-conjugated oils, or other oils. Non-conjugated oils, such as linseed oil, are fatty oils that contain polyunsaturated fatty acids, whose double bonds are separated by at least two single bonds. Conjugated oils on the other hand, such as tung oil, are polyunsaturated fatty acids whose double bonds are partly or fully conjugated.

Some faster drying non-conjugated polymerizing oils may be characterized as including alpha-linolenic acid. In an embodiment, the polymerizing oil is characterized as having at least 20% alpha-linolenic acid of unsaturated fatty acid content. In terms of its structure, alpha-linolenic acid is named all-cis-9,12,15-octadecatrienoic acid. In physiological literature, it is given the name C18:3 (n-3). Alpha-linolenic acid is a carboxylic acid with an 18-carbon chain and three cis double bonds. Other 18-carbon chain fatty acids may also be present in the polymerizing oil.

In some embodiments, the initial autoxidation step in non-conjugated oils (e.g. linseed), is dehydrogenation of the unsaturated fatty acid by oxygen, which forms a radical. This starts a radical chain reaction that increases incrementally with time, leading to the formation of a hydroperoxide. At low levels, the hydroperoxides produced during autoxidation, decompose to form free alkoxy and hydroxyl radicals. Higher levels of hydroperoxides form free radicals through boimolecular disproportionation. The resultant free radicals react in various ways to accelerate the autoxidation process. Accordingly, it is expected that a high degree of unsaturation of the fatty acid content, and particularly, high content of alpha-linolenic acid may correlate to being more conducive to skin formation, in accordance with some embodiments of the invention.

The drying of tung oil (a conjugated oil) varies considerably from linseed oil (a non-conjugated oil). Tung oil typically absorbs approximately 12% oxygen (linseed oil absorbs approximately 16%) and quickly forms a skin on the surface. Since less oxygen is absorbed, the viscosity of the oil can increase at a faster rate. Unlike the hydroperoxide formation during autoxidation in linseed oil, tung oil forms cyclic peroxides. (The methyl eleostearate formed has a higher molecular mass than linoleic acid esters). The direct attack on the double bonds by oxygen forms cyclic peroxides. The resultant reaction of the peroxides with allylic methylene groups, leads to the formation of radicals. This creates a radical chain reaction that forms polymers.

An iodine value, or iodine adsorption value, may be used to characterize drying oils, and in particular those including unsaturated fatty acids. Iodine value is the mass of iodine in grams that is consumed by 100 grams of a chemical substance, and may be used to determine the amount of unsaturation in fatty acids. This unsaturation is in the form of double bonds, which react with iodine compounds. The higher the iodine number, the more carbon-carbon double bonds are present in the fat. Oils with an iodine number of greater than 130 are typically considered drying oils, and whose with an iodine number of 115-130 are considered semi-drying, and those with an iodine number of less than 115 are non-drying.

However, iodine value is not always a precise indicator of drying ability. Tung oil and oiticia oil are characterized as conjugated acid oils, where iodine value is not as significant measurement of because conjugated acids do not absorb halogens. Iodine value is not necessarily a measure of drying ability because drying is based on conjugation of the oil not the amount of unsaturation of the oil. For example, the fatty acids/triglycerides of tung and oiticica oils contain three double bonds in conjugated sequence and which may result in oxidation drying and more robust skin formation than many drying oils with alpha-linolenic acids which have three double bonds but are not conjugated.

Table 1 includes a non-exclusive list of exemplary polymerizing oils that may be used in accordance with embodiments of the invention, along with iodine value, and percent alpha-linolenic acid of unsaturated fatty acid content. It is to be appreciated that the list of exemplary polymerizing oils is a non-exclusive list of oils that may readily oxidize and form a skin. However, selection of the appropriate polymerizing oil and drying conditions may be dependent upon system requirements and dimensions. For example, it is possible that some polymerizing oils may form a skin that is too hard for a specific delivery system.

TABLE 1

|  | Iodine value | Alpha-linolenic acid (C18:3) % |
| --- | --- | --- |
| Linseed oil | 170-204 | 35-60 |
| Soybean oil | 120-148 | 5-11 |
| Sunflower oil | 125-144 | — |
| Poppy seed oil | 133 | 11 |
| Perilla oil | 193-208 | 62-65 |
| Walnut oil | 143-148 | 3-8 |
| Hemp seed oil | 140-175 | 24-26 |
| Niger seed oil | 125-135 | 45-66 |

TABLE 1-continued

|  | Iodine value | Alpha-linolenic acid (C18:3) % |
| --- | --- | --- |
| Rubber seed oil | 132-148 | 21-26 |
| Chia oil | 190-199 | 64 |
| Kiwi seed oil | 170-205 | 62 |
| Lingonberry oil |  | 49 |
| Camelina oil | 127-155 | 35-45 |
| Purslane oil |  | 35 |
| Sea buckthorn oil | 130-200 | 32 |
| Candlenut oil | 135-166 | 28 |
| Safflower oil | 140-150 | 1 |
| Tall oil | 120-155 | 1-3 |
| *Stillingia* oil | 169-191 | 40 |
| Tung oil | 160-175 | * |
| Oiticica oil | 150 | ** |

* alpha-eleostearic acid 80%, alpha-lenolenic acid 3%.
** 73% conjugated acids, 16% unsaturated acids In the following description of Examples 1 and 2, the results of two tests are described which illustrate the use of a polymerizing oil to form a seal around a hydrogel or seal the distal end of a catheter sheath to prevent premature swelling of the hydrogel in accordance with embodiments of the invention.

Example 1

Boiled liquid linseed oil containing less than 1% cobalt containing drying agent and less than 1% manganese containing drying agent (KLEAN-STRIP® Boiled Linseed Oil, available from W.M. Barr & Company, Inc. of Memphis, Tenn., USA) was drawn from the 3.785 liter manufacturer container into a syringe, though the polymerizing oil could have been drawing into a number of alternative dispensing containers, such as an engineering fluid dispenser (EFD). A sufficient amount of liquid linseed oil was dispensed onto the occlusion device illustrated in FIG. 1A to coat the hydrogels 110. The occlusion device was then hung proximal side up, distal side down, for 24 hours at ambient conditions (room temperature, pressure, atmosphere). During this time the linseed oil formed an outer skin. The coated occlusion device was then immersed in a beaker filled with water, and removed after 7 minutes of immersion in water.

Figure 3A:
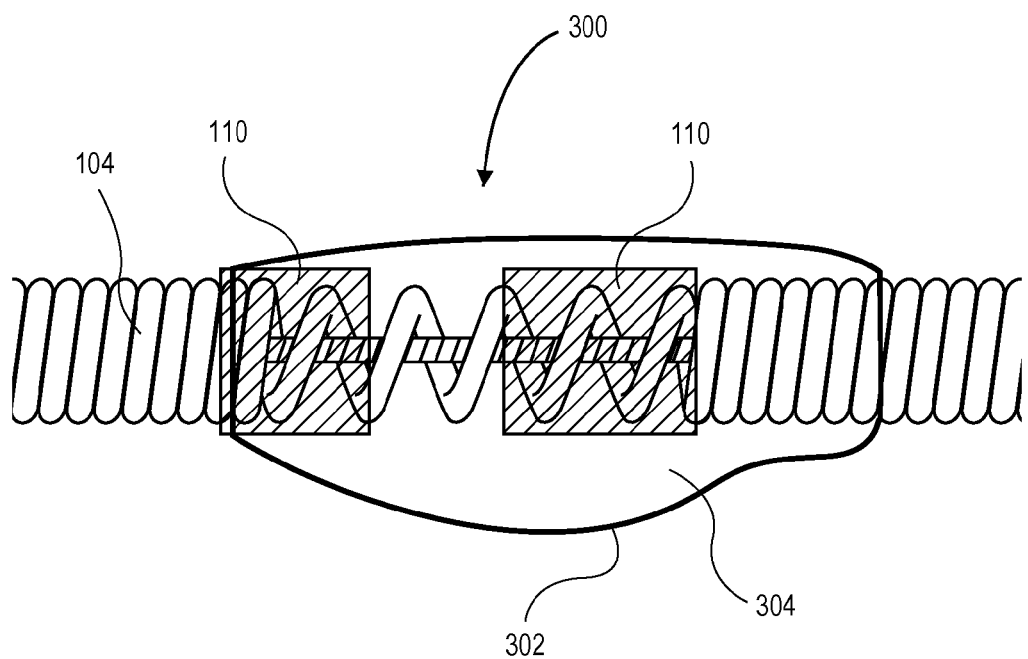
FIG. 3A is schematic side view illustration of an occlusion device coated with a polymerizing oil after 24 hours at ambient conditions in accordance with an embodiment of the invention.

FIG. 3A is a schematic side-view illustration of the coated occlusion device after 24 hours at ambient conditions. As shown, after 24 hours at ambient conditions the linseed oil 300 quantity formed a cross-linked skin 302 as a result of oxidation. In this example, the skin 302 additionally encapsulated a liquid portion 304 of the linseed oil. The skin staying in place was observed to be elastic and deformable to the touch. It was also observed that the linseed oil 300 did not completely cover the proximal end of the proximal hydrogel 110.

Figure 3B:
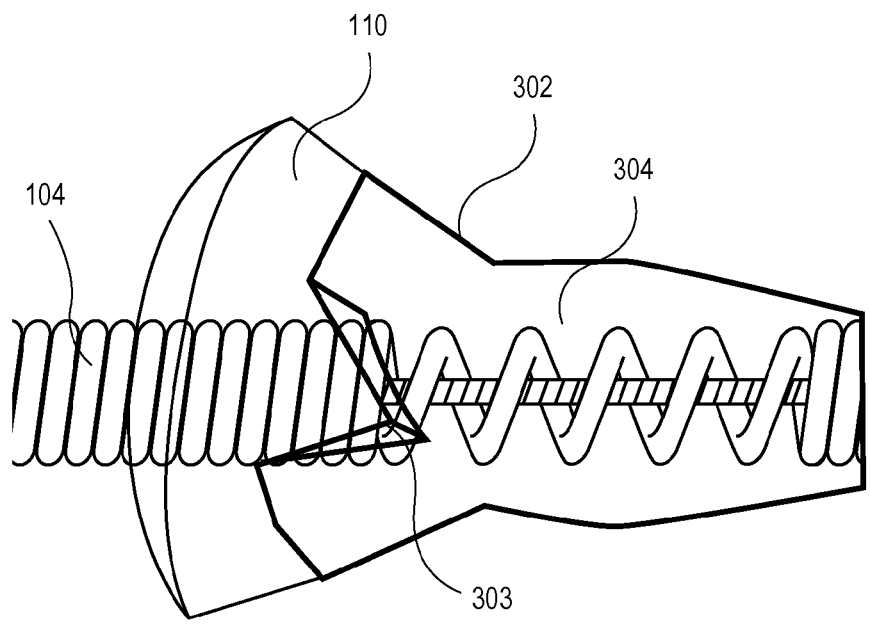
FIG. 3B is a schematic side view illustration of the coated occlusion device of FIG. 3A after immersion in water for 7 minutes in accordance with an embodiment of the invention.

FIG. 3B is a schematic side-view illustration of the coated occlusion device after immersion in water for 7 minutes. As illustrated, the proximal end of the proximal hydrogel 110 began to hydrate, while the distal portion of the proximal hydrogel 110, and the distal hydrogel 110 did not hydrate. Furthermore, upon closer examination, a split 303 was visible in the coating where the proximal end of the proximal hydrogel 110 increased in size.

The results of Example 1 illustrate that a polymerizing oil can be applied to a hydrogel and allowed to oxidize at ambient conditions to form a protective skin that protects the hydrogel from premature swelling. Furthermore, the results of Example 1 illustrate that the protective skin while strong enough to protect against migration of the drying oil, can be split where the hydrogel is allowed to absorb water and swell.

Example 2

Boiled liquid linseed oil containing less than 1% cobalt containing drying agent and less than 1% manganese containing drying agent (KLEAN-STRIP® Boiled Linseed Oil, available from W.M. Barr & Company, Inc. of Memphis, Tenn., USA) was drawn from the 3.785 liter manufacturer container into a syringe, though the polymerizing oil could have been drawing into a number of alternative dispensing containers, such as an EFD. A sufficient amount of liquid linseed oil was injected into the lumen of the distal end of the catheter sheath of the delivery system illustrated in FIG. 2 to form a protective cap distal to the distal end of the distal hydrogel illustrated in FIG. 1A. The delivery system was then hung on a catheter tree proximal side up, distal side down, for 24 hours at ambient conditions (room temperature, pressure, atmosphere). It is believed that capillary forces initially retained the linseed oil inside the catheter sheath and prevented the linseed oil from dripping out of the distal end of the catheter sheath, which was pointing down. During this time the linseed oil formed an outer skin. The distal end of the delivery system including the occlusion device, catheter sheath, and linseed oil was then immersed in a beaker filled with water, and removed after 40 minutes of immersion in water. The catheter sheath was then rolled back to expose the portion of the occlusion device including the pair of hydrogel sleeves 110.

Figure 4A:
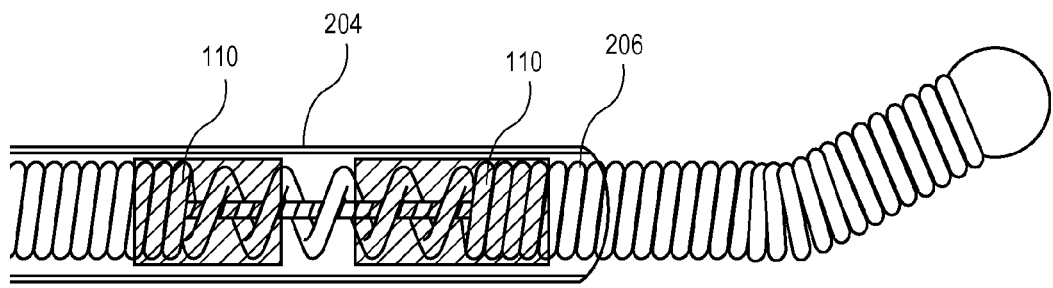
FIG. 4A is a schematic side-view illustration of the distal end of the delivery system illustrated in FIG. 2 prior to injecting the liquid linseed oil into the lumen of the catheter sheath in accordance with an embodiment of the invention.
Figure 4B:
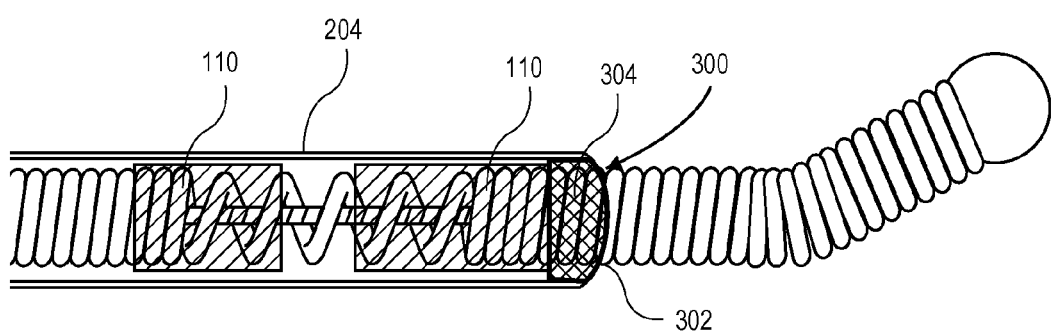
FIG. 4B is a schematic side-view illustration of the distal end of the delivery system after the linseed oil had been injected and the delivery system had been hung on the catheter tree proximal side up, distal side down, for 24 hours at ambient conditions in accordance with an embodiment of the invention.

FIG. 4A is a schematic side-view illustration of the distal end of the delivery system illustrated in FIG. 2 prior to injecting the liquid linseed oil into the lumen of the catheter sheath. As illustrated, the hydrogel sleeves 110 are located within the lumen 206 of the catheter sheath 204. FIG. 4B is a schematic side-view illustration of the distal end of the delivery system after the linseed oil had been injected and the delivery system had been hung on the catheter tree proximal side up, distal side down, for 24 hours at ambient conditions. As shown, after 24 hours at ambient conditions the linseed oil quantity 300 formed a cross-linked skin 302 as a result of oxidation. In this example, the skin 302 encapsulated a liquid portion 304 of the linseed oil. The skin staying in place was observed to be elastic and deformable to the touch. In the particular embodiment illustrated, the quantity of linseed oil 300 was located between the distal end of the catheter sheath 204 and the distal hydrogel 110. In such an embodiment, the quantity of linseed oil 300 formed a plug distal to the distal hydrogel 110, and the linseed oil was not substantially formed over the hydrogels 110. In this manner, it is expected that this configuration will allow for unobstructed swelling of the hydrogels after rollback of the catheter sheath 204 in vivo. In other embodiments, the quantity of linseed oil 300 may be allowed to partially or completely wick over one or more hydrogels 110.

Figure 4C:
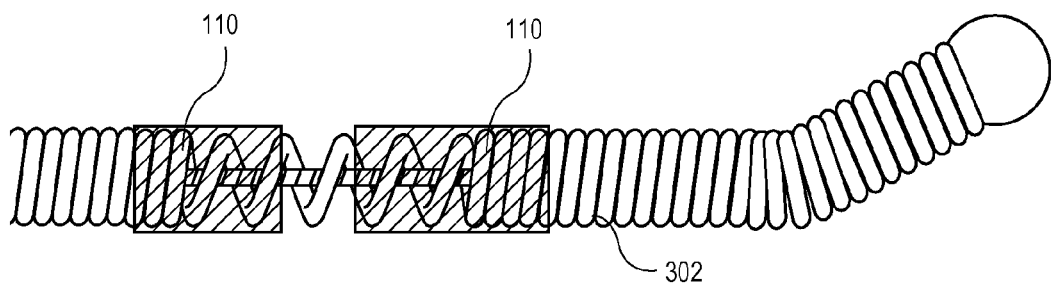
FIG. 4C is a schematic side-view illustration of the delivery system after immersion in water for 40 minutes and rollback of the catheter sheath 204 to expose the distal portion of the occlusion device including the pair of hydrogel sleeves 110 in accordance with an embodiment of the invention.

FIG. 4C is a schematic side-view illustration of the delivery system after immersion in water for 40 minutes and rollback of the catheter sheath 204 to expose the distal portion of the occlusion device including the pair of hydrogel sleeves 110. As illustrated, the proximal and distal hydrogels 110 did not hydrate, and remained in their deswollen shapes. Rollback of the catheter sheath 204 occurred without issue. In addition, after rollback portions of the cross-linked skin 302 were observed to remain on the inner coil 104 of the expandable implant.

The results of Example 2 illustrate that polymerizing oil can be injected into a distal end of a catheter sheath to cap or seal the lumen at the distal end of the catheter in order to protect against premature swelling of hydrogels within the catheter sheath. The results of Example 2 additionally illustrate that the protective skin while strong enough to protect against migration of the drying oil and liquid penetration into the lumen of the catheter sheath, the protective skin also does not affect catheter sheath rollback and can be split or torn upon catheter rollback to expose the hydrogels. Furthermore, it is expected that this configuration will allow for unobstructed swelling of the hydrogels after rollback of the catheter sheath 204 in vivo.

Figure 5A:
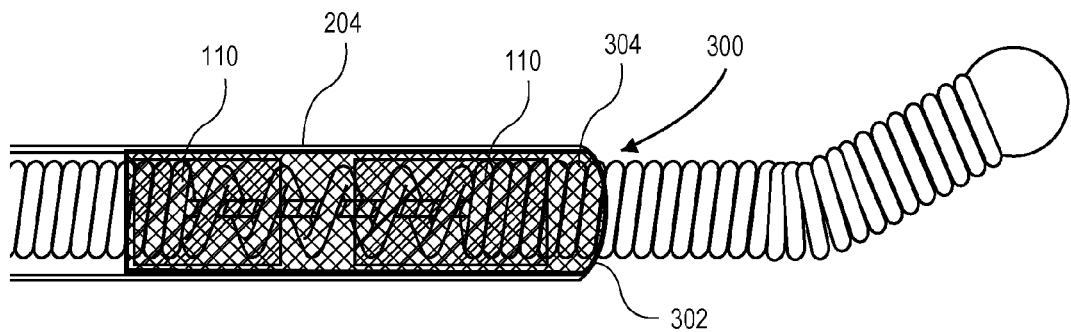
FIG. 5A is a schematic side-view illustration of polymerizing oil injected into the distal end of a catheter sheath an allowed to wick around proximally of the proximal hydrogel in accordance with an embodiment of the invention.
Figure 5B:
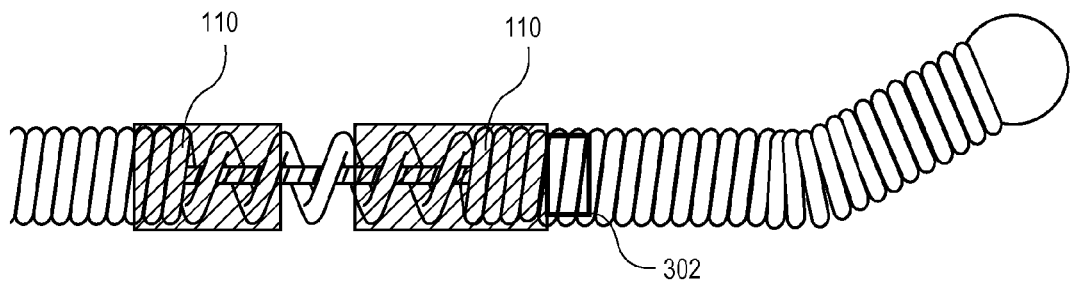
FIG. 5B is a schematic side-view of the skin of the polymerizing oil remaining on the inner coil and removed from the radial surfaces of the hydrogel sleeves after rollback of the catheter sheath in accordance with an embodiment of the invention.
Figure 5C:
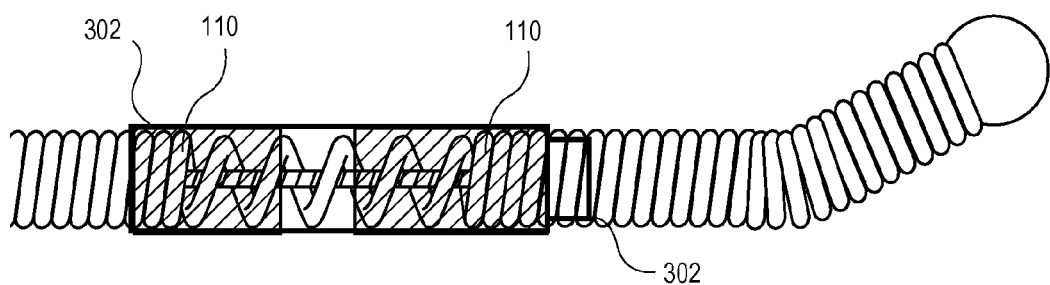
FIG. 5C is a schematic side-view of the skin of the polymerizing oil remaining on the inner coil and radial surfaces of the hydrogel sleeves after rollback of the catheter sheath in accordance with an embodiment of the invention.

FIGS. 5A-5C illustrate additional embodiments of the invention, in which similar to Example 2, a liquid polymerizing oil can be injected into the distal end of a catheter sheath 204, for example, by using a syringe or EFD. In an embodiment, the liquid polymerizing oil is allowed to at least partially wick around the one or more hydrogels. In the particular embodiment illustrated in FIG. 5A, the polymerizing oil is allowed to wick around both hydrogels 110, and proximally of the proximal hydrogel 110. The polymerizing oil can then be allowed to oxidize to form outer skin 302 as previously described. In the embodiment illustrated in FIG. 5A, the polymerizing oil and skin 302 may encapsulate the one or more hydrogels 110.

FIGS. 5B-5C illustrate alternative results upon rolling back the catheter sheath of FIG. 5A. In the embodiment illustrated in FIG. 5B, the skin 302 of the polymerizing oil may remain on the inner coil 104 of the occlusion device but be removed, at least partially, from the radial surfaces of the hydrogel sleeves 110 that were adjacent the catheter sheath 204. In such an embodiment, the skin 302 adjacent the catheter sheath 204 may be withdrawn with the sheath or torn by withdrawal of the sheath to expose the hydrogel sleeves 110. In the embodiment illustrated in FIG. 5C, the skin 302 of the polymerizing oil may remain on the inner coil 104 of the occlusion device as well as on the radial surfaces of the hydrogel sleeves 110.

In one implementation, the result of FIG. 5B may be incorporated into a delivery system design in which the skin 302 is designed to be removed from the expanding surfaces of the hydrogel sleeves 110 so as to not interfere with the ability of the hydrogel sleeves 110 to swell and provide immediate or near immediate occlusion in vivo. In another implementation, the result of FIG. 5C may be incorporated into a delivery system design in which the skin 302 is designed to remain on the hydrogel sleeves and function as a timed expansion control element. In an embodiment, the skin 302 may be bioabsorbable or bioerodible so that it is removed over time. A bioabsorbable or bioerodible skin may also be beneficial to remove fragments of the skin that may be inadvertently left behind adjacent a hydrogel.

In accordance with embodiments of the invention the polymerizing oils may be formulated to endure a specific amount of oxidation or achieve specific skin characteristics such as hardness (flexibility), thickness, and tear strength. As described above, a polymerizing oil may be selected based upon its iodine value, degree of unsaturation, alphalenolenic acid content, or amount of conjugation since these may be used to indicate the propensity for oxidation and skin formation of the polymerizing oil. Oxidation and skin formation may also be controlled by exposure time to air, or controlling the atmosphere or temperature of the atmosphere the polymerizing oil is exposed to. For example, elevated temperatures or elevated oxygen levels may increase the amount of oxidation, and resultantly the amount of skin formation which can correlate to thickness or hardness of the skin, as well as the amount of liquid polymerizing oil encapsulated by the skin. In addition, the grade of drying oil and additives may be selected to achieve the desired amount of skin formation. In an embodiment, an oil drying agent or siccative can be added to the polymerizing oil to promote oxidation. For example, a drying agent may be a metal coordination complexes with a carboxylic acid derivate. Common drying agents include carboxylates of zirconium, zinc, calcium, cobalt, manganese, and iron. Fatty acid metal salts such as cobalt or manganese naphthenates are also commonly used. Grade of the drying oil may also affect the resultant skin properties. For example, linseed oil is available in raw, refined, boiled, cold-pressed, stand, sun-thickened, and hydrogenated grades.

Figure 6:
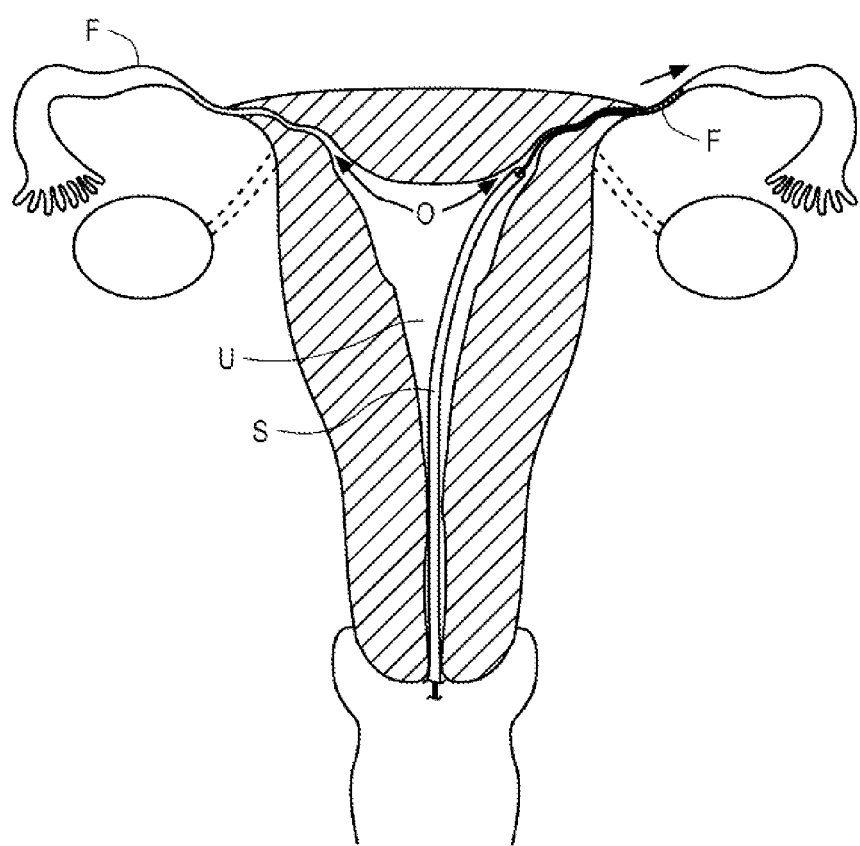
FIGS. 6-10 illustrate a method of delivering an occlusion device to a fallopian tube and facilitating immediate, or near immediate, and permanent sterilization in accordance with an embodiment of the invention.

FIGS. 6-10 illustrate a method of delivering an occlusion device to a fallopian tube and facilitating immediate, or near immediate, and permanent sterilization. Referring now to FIG. 6, a delivery system S, such as delivery system 200 is introduced transcervically through uterus U, generally under optical direction. The physician directs the distal end of the delivery system toward the ostium O of the fallopian tube F. The uterus U may be irrigated and/or distended. Once the ostium O is located and the delivery system S is oriented toward the ostium, the delivery system S is advanced distally into the ostium.

Figure 7:
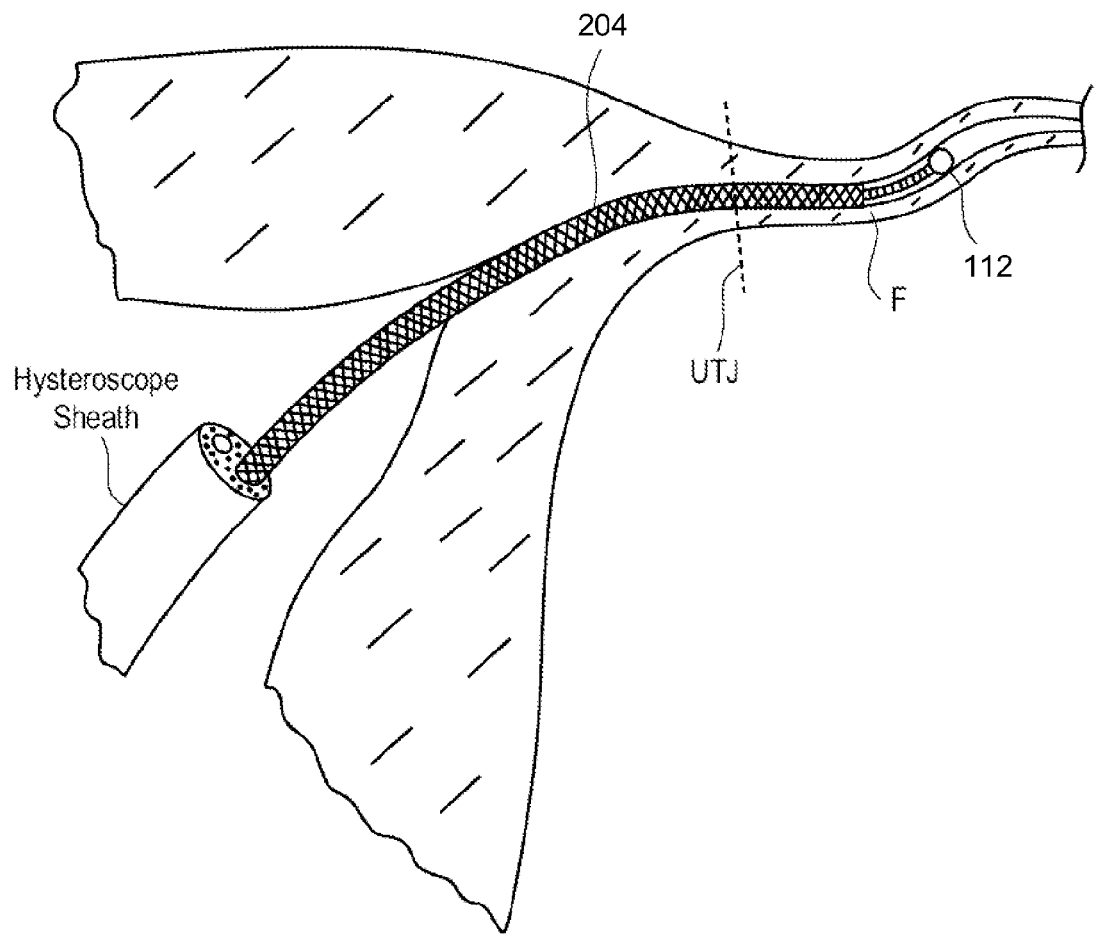

In one embodiment, the distal portion of the occlusion device acts as a guidewire, while the remainder of the occlusion device remains covered by the sheath 204, as shown in FIG. 7. The distal ball tip 112 of the distal portion of the occlusion device aids tracking and navigation through the fallopian tube F, while the inner coil structure flexes laterally to track the tortuous bends often found within the fallopian tube. In the exemplary embodiment, a core wire extends into the distal portion to enhance column strength of the distal portion beyond sheath, but does not extend to the ball tip. Hence, the stiffness of distal portion increases proximally, further enhancing the distal portion's ability to track the lumen. In another embodiment, the occlusion device will be entirely within the sheath 204 during delivery and positioning.

In the exemplary embodiment, the sheath includes a visual marker which can be seen from the scope of an hysteroscope. The marker is preferably positioned partially within the ostium O and partially within the uterus U, thereby indicating that the occlusion device is disposed at the target position, as the sheath, core shaft, and occlusion device are releasably locked together during advancement and positioning. For example, the marker may comprise a bumper, or a structure which extends radially from the sheath to provide a tactile positioning indication.

Figure 8:
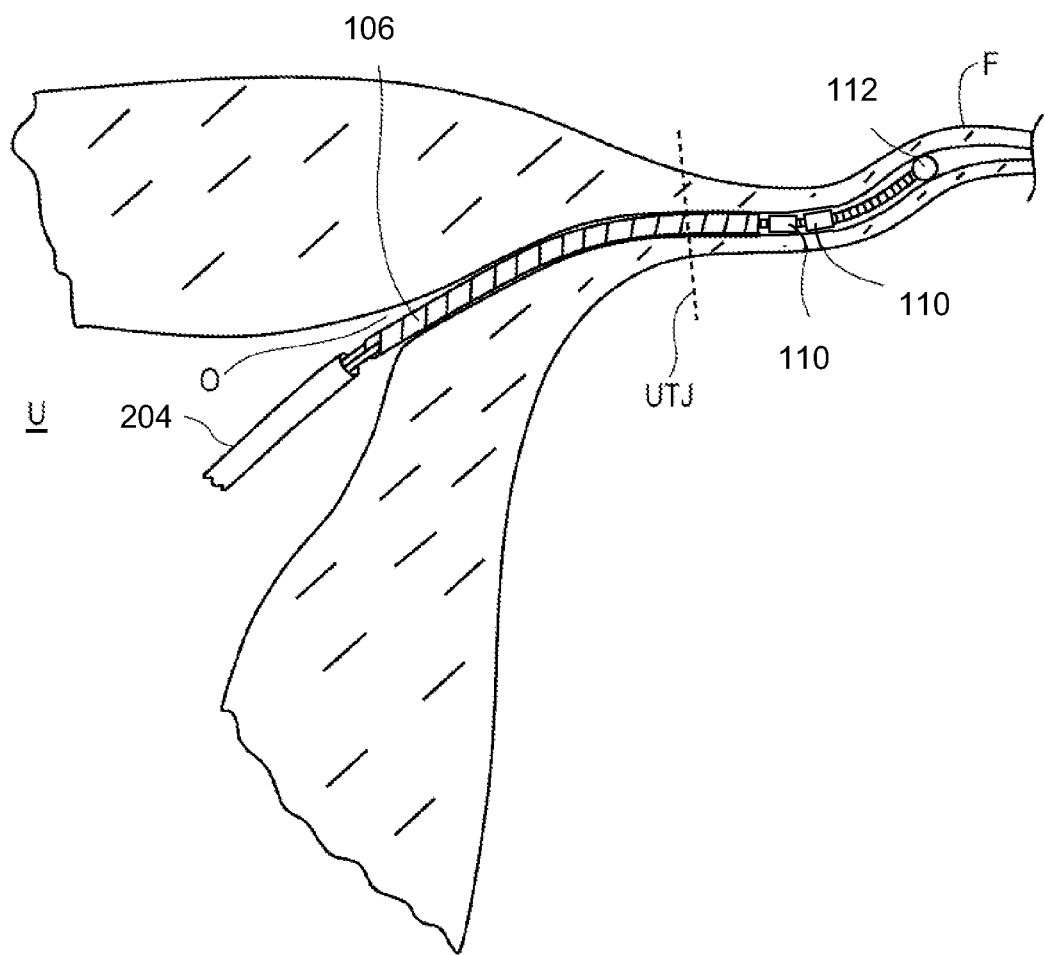
Figure 9:
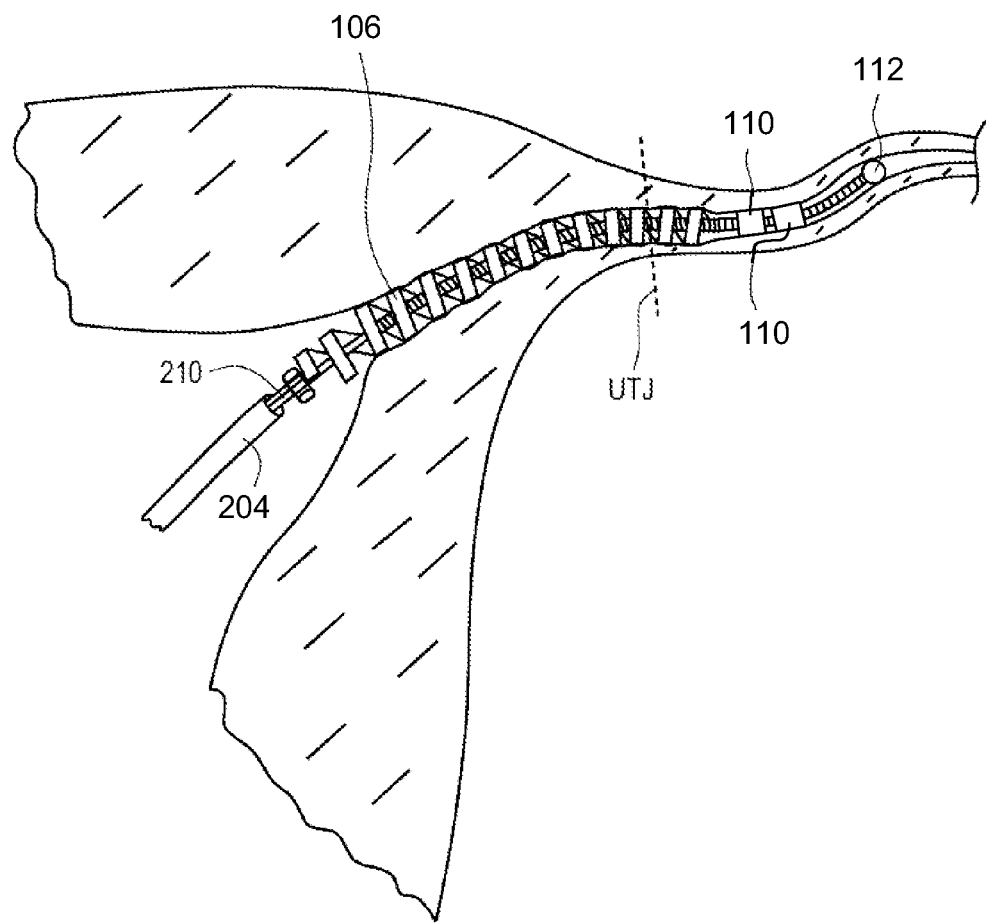
Figure 10:
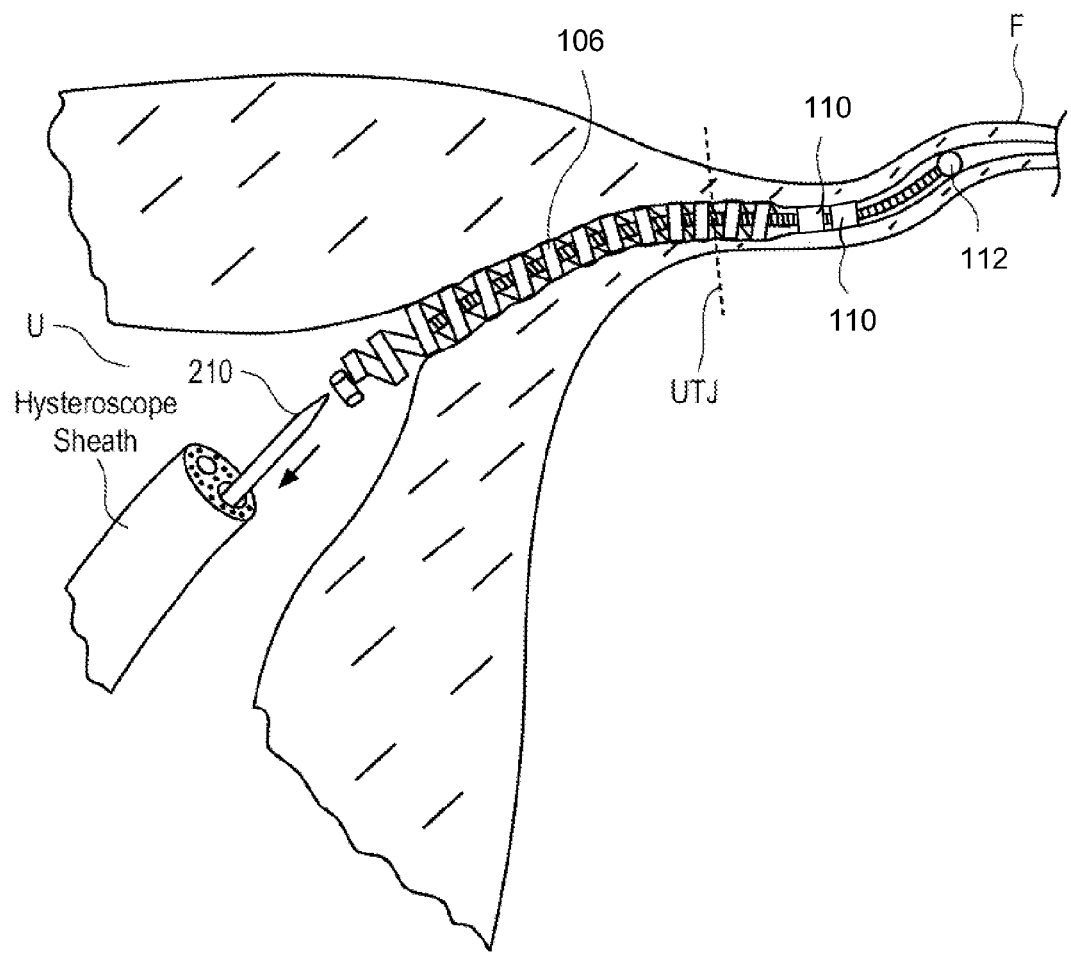

Referring now to FIGS. 8-9, the positioned occlusion device is deployed, in one embodiment, by first withdrawing the catheter sheath 204 from over the outer coil 106, as shown in FIG. 8. The outer coil 106 is then separated from the delivery wire 210, allowing the outer coil 106 to expand affix the occlusion device in place, as shown in FIG. 9. In one embodiment, withdrawal of the catheter sheath 204 tears the skin 302 within the lumen of the catheter sheath 204 exposing the radial, or expanding surfaces of the one or more hydrogels 110. The one or more hydrogels 110 have, at this point, begun to swell and will at least temporarily block the fallopian tube. The occlusion device is then separated from the remaining components of delivery system, as shown in FIG. 10, where the catheter sheath 204 and delivery wire 210 are withdrawn into a hysteroscope sheath. As shown in FIG. 10, the pair of hydrogels 110 may expand to fill in areas of the fallopian tube to block the fallopian tube. In another embodiment, the skin 302 may remain on the radial, or expanding surfaces of the one or more hydrogels 110 and function as a time expansion control element that is bioabsorbable or bioerodible over time.

In the foregoing specification, various embodiments of the invention have been described. It will, however, be evident that various modifications and changes may be made thereto without departing from the broader spirit and scope of the invention as set forth in the appended claims. The specification and drawings are, accordingly, to be regarded in an illustrative sense rather than a restrictive sense. Hence, the scope of the present invention is limited solely by the following claims.

What is claimed is:

1. A delivery system comprising:
   a catheter sheath having a distal end, a proximal end, and a lumen therebetween;
   an occlusion device releasably coupled within the catheter sheath, the occlusion device comprising an expandable implant and at least one hydrogel sleeve on the expandable implant including a distal hydrogel sleeve having a distal end; and
   a polymerizing oil inside a portion of the lumen of the catheter sheath between the distal end of the catheter sheath and the distal end of the distal hydrogel sleeve, wherein the polymerizing oil is at least partially oxidized to form a plug within the catheter sheath, at a location distal to the distal hydrogel sleeve.

2. The delivery system of claim 1, wherein the polymerizing oil comprises a cross-linked skin.

3. The delivery system of claim 2, wherein the polymerizing oil protects the at least one hydrogel sleeve from swelling upon exposure of the distal end of the catheter sheath to a physiological environment.

4. The delivery system of claim 3, wherein the catheter sheath can be withdrawn to expose the at least one hydrogel sleeve.

5. The delivery system of claim 4, wherein the cross-linked skin can be torn by withdrawal of the catheter sheath to expose the at least one hydrogel sleeve.

6. The delivery system of claim 2, wherein the polymerizing oil comprises an incompletely cured portion which is encapsulated by the cross-linked skin and the catheter sheath.

7. The delivery system of claim 2, wherein the polymerizing oil comprises oxidized alpha-linolenic acid.

8. The delivery system of claim 2, wherein the polymerizing oil is characterized as including at least 20% by weight alpha-linolenic acid as a percentage of fatty acid composition prior to being partially oxidized.

9. The delivery system of claim 8, wherein the polymerizing oil comprises linseed oil.

10. The delivery system of claim 2, wherein the polymerizing oil does not encapsulate a proximal end of the at least one hydrogel sleeve.

11. The delivery system of claim 2, wherein the polymerizing oil comprises a conjugated oil.

12. The delivery system of claim 11, wherein the conjugated oil is selected from the group consisting of tung oil and oiticica oil.

13. The delivery system of claim 2, wherein the polymerizing oil has an iodine value above 130.

14. The delivery system of claim 2, wherein the polymerizing oil partially encapsulates the distal hydrogel sleeve.

15. The delivery system of claim 2, wherein the catheter sheath extends beyond the distal hydrogel sleeve to form the portion of the lumen between the distal end of the catheter sheath and the distal end of the distal hydrogel sleeve.

16. The delivery system of claim 2, wherein the polymerizing oil is not substantially formed over the distal hydrogel sleeve.

17. The delivery system of claim 1, wherein the at least one hydrogel sleeve is a preformed hollow cylinder attached to the expandable implant.

18. The delivery system of claim 17, wherein the hollow cylinder is attached to the expandable implant with glue.

* * * * *